US012576014B2

(12) United States Patent
Loganathan et al.

(10) Patent No.: US 12,576,014 B2
(45) Date of Patent: Mar. 17, 2026

(54) PERSONAL CARE COMPOSITION WITH VISUALLY DISTINCT AQUEOUS AND OIL PHASE

(71) Applicant: Conopco, Inc., Englewood Cliffs, NJ (US)

(72) Inventors: Chandersekar Loganathan, Shanghai (CN); Yueyuan Pan, Shanghai (CN)

(73) Assignee: Conopco, Inc., Hoboken, NJ (US)

( * ) Notice: Subject to any disclaimer, the term of this patent is extended or adjusted under 35 U.S.C. 154(b) by 253 days.

(21) Appl. No.: 17/918,343

(22) PCT Filed: Apr. 20, 2021

(86) PCT No.: PCT/EP2021/060141
§ 371 (c)(1),
(2) Date: Oct. 12, 2022

(87) PCT Pub. No.: WO2021/228503
PCT Pub. Date: Nov. 18, 2021

(65) Prior Publication Data

US 2023/0137330 A1 May 4, 2023

(30) Foreign Application Priority Data

May 9, 2020 (WO) ................ PCT/CN2020/089331
Jun. 18, 2020 (EP) .................................... 20180672

(51) Int. Cl.
*A61K 8/37* (2006.01)
*A61K 8/03* (2006.01)
*A61K 8/34* (2006.01)
*A61Q 19/02* (2006.01)

(52) U.S. Cl.
CPC ................ *A61K 8/03* (2013.01); *A61K 8/345* (2013.01); *A61K 8/347* (2013.01); *A61K 8/37* (2013.01); *A61Q 19/02* (2013.01); *A61K 2800/262* (2013.01); *A61K 2800/87* (2013.01); *A61K 2800/882* (2013.01)

(58) Field of Classification Search
CPC ... A61K 8/34; A61K 8/49; A61K 8/67; A61Q 19/02; A61Q 19/08
See application file for complete search history.

(56) References Cited

U.S. PATENT DOCUMENTS

| | | | | |
|---|---|---|---|---|
| 3,810,478 | A | 5/1974 | Olson, Jr. et al. | |
| 4,826,828 | A | 5/1989 | Wilmott et al. | |
| 4,888,363 | A | 12/1989 | Dulak et al. | |
| 4,992,265 | A | 2/1991 | Davis et al. | |
| 5,599,548 | A | 2/1997 | Granger et al. | |
| 5,811,110 | A | 9/1998 | Granger et al. | |
| 5,880,314 | A | 3/1999 | Shinomiya et al. | |
| 11,389,382 | B2 * | 7/2022 | Peel | A61K 8/37 8/347 |
| 2003/0165546 | A1 | 9/2003 | Resch et al. | |
| 2005/0238680 | A1 | 10/2005 | Stella et al. | |
| 2006/0008438 | A1 | 1/2006 | Velarde et al. | |
| 2006/0078524 | A1 | 4/2006 | Midha et al. | |
| 2006/0078527 | A1 | 4/2006 | Midha et al. | |
| 2006/0079417 | A1 | 4/2006 | Wagner et al. | |
| 2006/0210612 | A1 | 9/2006 | Simon et al. | |
| 2007/0009446 | A1 | 1/2007 | Romero | |
| 2007/0117729 | A1 | 5/2007 | Taylor et al. | |
| 2008/0299058 | A1 | 12/2008 | Saito et al. | |
| 2009/0196836 | A1 | 8/2009 | Tanner et al. | |
| 2010/0068307 | A1 | 3/2010 | Nielloud | |
| 2011/0082217 | A1 | 4/2011 | Johnson et al. | |
| 2012/0276177 | A1 | 11/2012 | Hilliard, Jr. et al. | |
| 2013/0251644 | A1 | 9/2013 | Majhi et al. | |
| 2014/0147525 | A1 | 5/2014 | de Paula et al. | |
| 2016/0256367 | A1 | 9/2016 | Charbit | |
| 2016/0324869 | A1 | 11/2016 | Wei et al. | |
| 2017/0087064 | A1 | 3/2017 | Ikeda et al. | |
| 2018/0161259 | A1 | 6/2018 | Ha et al. | |
| 2018/0177695 | A1 | 6/2018 | Miller et al. | |
| 2018/0360705 | A1 | 12/2018 | Alam et al. | |
| 2019/0142706 | A1 | 5/2019 | Sverdlove et al. | |
| 2019/0336421 | A1 | 11/2019 | Maruyama | |

FOREIGN PATENT DOCUMENTS

| | | |
|---|---|---|
| CN | 1377403 | 10/2002 |
| CN | 1237898 | 1/2006 |
| CN | 1946375 | 4/2007 |
| CN | 103202775 | 7/2013 |
| CN | 104640534 | 5/2015 |
| CN | 106580755 | 4/2017 |

(Continued)

OTHER PUBLICATIONS

Leszek Marszall; Messungen des effektiven HLB-Wertes nichtionogener Tenside mittels Phenol-Titrationsmethode; Parfumerie und Kosmetik; 1979; PP444-448—with English translation; vol. 60; Germany.

(Continued)

*Primary Examiner* — Robert A Wax
*Assistant Examiner* — Kimberly Barber
(74) *Attorney, Agent, or Firm* — Stephanie Huang

(57) ABSTRACT

Disclosed is a multi-phase personal care composition comprising an aqueous phase, and an oil phase comprising fatty ester and resorcinol derivative, wherein the weight ratio of the fatty ester to the resorcinol derivative is from 10:1 to 1000:1 and the aqueous phase is visually distinct from and in physical contact with the oil phase.

20 Claims, No Drawings

(56) References Cited

FOREIGN PATENT DOCUMENTS

| | | |
|---|---|---|
| CN | 107997996 | 5/2018 |
| CN | 108367179 | 8/2018 |
| CN | 108524322 | 9/2018 |
| CN | 109248102 | 1/2019 |
| CN | 109310591 | 2/2019 |
| CN | 111000735 | 4/2020 |
| DE | 2358822 | 6/1975 |
| DE | 9216886 | 4/1994 |
| DE | 19501184 | 7/1996 |
| DE | 102013226276 | 7/2014 |
| EP | 1676560 | 7/2006 |
| FR | 2252403 | 6/1975 |
| FR | 2645740 | 10/1990 |
| FR | 2835430 | 8/2003 |
| JP | S62135404 | 6/1987 |
| JP | H01294615 | 11/1989 |
| JP | H11209235 | 8/1999 |
| JP | 200095721 | 4/2000 |
| JP | 2002284626 | 3/2001 |
| JP | 2002255739 | 9/2002 |
| JP | 2010280593 | 12/2010 |
| JP | 2011001270 | 1/2011 |
| JP | 2015229634 | 12/2015 |
| JP | 2018140960 | 9/2018 |
| WO | WO8606275 | 11/1986 |
| WO | WO9622072 | 7/1996 |
| WO | WO9807406 | 2/1998 |
| WO | WO0123514 | 4/2001 |
| WO | WO2005105033 | 11/2005 |
| WO | WO2006042176 | 4/2006 |
| WO | WO2014013420 | 1/2014 |
| WO | WO2017110151 | 6/2017 |
| WO | WO2017220310 | 12/2017 |
| WO | WO2018114232 | 6/2018 |
| WO | WO2019011619 | 1/2019 |
| WO | WO2021228492 | 11/2021 |
| WO | WO2021228502 | 11/2021 |
| WO | WO2021228519 | 11/2021 |

OTHER PUBLICATIONS

Dr. Otto-Albrecht Neumuller; Franck'sce Verlagshandlung, Stuttgart; Rompps Chemie-Lexikon; 1983; pp. 1750-1751, with English translation; 8th Edition; Germany.

Search Report and Written Opinion in EP20180662; Dec. 14, 2020; European Patent Office (EPO).

Database GNPD (Online) Mintel; Once and No Makeup 2-Phase Make-up Remover; Nature.Med Tonik; Sep. 2017; pp. 1-3, Record ID 5111633, XP055754195; Ukraine.

Database GNPD (Online) Mintel; Renew & Repair Solution; Beauty Drops; Mar. 2019; pp. 1-5, Record ID 6432731, XP055754197; Spain.

Search Report and Written Opinion in EP20180664; Dec. 14, 2020; European Patent Office (EPO).

Search Report and Written Opinion in PCTEP2021060141; Jul. 7, 2021; World Intellectual Property Org. (WIPO).

Database GNPD (Online) Mintel; Bouncy Skin Kit; Glow Recipe; Jun. 2020; pp. 1-6, Record ID 7904250, XP055754204; United Kingdom.

Database GNPD (Online) Mintel; VitaC Glycolic Brightening Serum; Murad Environmental Shield; Mar. 2020; pp. 1-6, Record 7452259, XP055754208; .; United States of America.

Search Report and Written Opinion in PCTEP2021059985; Jul. 7, 2021; World Intellectual Property Org. (WIPO).

Search Report and Written Opinion in EP20180677; Dec. 14, 2020; European Patent Office (EPO).

Search Report and Written Opinion in EP20180672; Dec. 14, 2020; European Patent Office (EPO).

Search Report and Written Opinion in PCTEP2021060317; Jul. 5, 2021; World Intellectual Property Org. (WIPO).

Search Report and Written Opinion in PCTEP2021060140; Jul. 5, 2021; World Intellectual Property Org. (WIPO).

IPRP2 in PCTEP2021060140; Apr. 25, 2022; World Intellectual Property Org. (WIPO).

Written Opinion 2 in PCTEP2021060141; Apr. 25, 2022; World Intellectual Property Org. (WIPO).

IPRP2 in PCTEP2021060141; Jun. 24, 2022; World Intellectual Property Org. (WIPO).

Written Opinion 2 in PCTEP2021060317; Mar. 31, 2022; World Intellectual Property Org. (WIPO).

IPRP2 in PCTEP2021060317; May 10, 2022; World Intellectual Property Org. (WIPO).

IPRP2 in PCTEP2021059985; May 17, 2022; World Intellectual Property Org. (WIPO).

Written Opinion 2 in PCTEP2021059985; Mar. 24, 2022; World Intellectual Property Org. (WIPO).

Database GNPD (Online) Mintel; Oil Shaker Dual Phase Refining Oil; Decorté Phytotune; Sep. 2019; pp. 1-3, Record ID 6874605; Japan.

Database GNPD (Online) Mintel; Biphase Make-Up Remover; Vinésime Racine du Temps; May 2019; pp. 1-3, Record ID 6494461; France.

Database GNPD (Online) Mintel; Anti/Oxi+ Clarifying Gentle Cleansing Oil in Water; Shu Uemura Skin Purifier; Nov. 2018; pp. 1-4, Record ID 6118721; Japan.

Database GNPD (Online) Mintel; Eye Makeup Remover; Neutrogena Deep Clean; Sep. 2016; pp. 1-2, Record ID 4277647; Greece.

Database GNPD (Online) Mintel; Biphasic Hydrating Cleansing; Violetta Rostro y Ojos; Mar. 2015; pp. 1-2, Record ID 3046791; Argentina.

Ma Zhenyou; Manual of Cosmetic Preparations for Skin Beauty; Publishing House of Traditional Chinese Medical Books; Jan. 31, 2015; pp. 471-472, with English translation.

* cited by examiner

PERSONAL CARE COMPOSITION WITH VISUALLY DISTINCT AQUEOUS AND OIL PHASE

CROSS REFERENCE TO RELATED APPLICATIONS

The present application is a U.S. National Phase Application under 35 U.S.C. § 371 of International Application No. PCT/EP2021/060141, filed on Apr. 20, 2021, which claims priority to International Application No. PCT/CN2020/089331, filed on May 9, 2020, and European Patent Application No. 20180672.6, filed on Jun. 18, 2020, the contents of which are incorporated herein in their entireties.

FIELD OF THE INVENTION

The present invention relates to a multi-phase personal care composition. In particular, the present invention relates to a multi-phase personal care composition comprising an aqueous phase, and an oil phase comprising fatty ester and resorcinol derivative, wherein the aqueous phase is visually distinct from and in physical contact with the oil phase.

BACKGROUND OF THE INVENTION

Resorcinol derivatives have cosmetic skin and hair benefits. Certain resorcinol derivatives, particularly 4-substituted resorcinol derivatives, are useful in cosmetic compositions for skin lightening benefits.

However, when resorcinol derivatives are incorporated into personal care compositions, the color of the composition tend to change due to many factors. Without being bound by theory, one hypothesis for the cause of discoloration is due to oxidation. The discoloration of resorcinol derivatives useful in skin lightening compositions, is especially distasteful to consumers seeking skin lightening benefits. Many attempts have been made to minimize these drawbacks, but so far with minimal success.

There is a need, therefore, for a way that will prevent the esthetically displeasing discoloration of resorcinol derivatives in personal care compositions. The present inventors developed a multi-phase personal care composition comprising resorcinol derivative in the oil phase which is visually distinct from the aqueous phase. It was surprisingly found that the problem of discoloration is significantly improved by incorporating fatty ester into the oil phase.

SUMMARY OF THE INVENTION

In a first aspect, the present invention is directed to multi-phase personal care composition comprising an aqueous phase, and an oil phase comprising fatty ester and resorcinol derivative, wherein the weight ratio of the fatty ester to the resorcinol derivative is from 10:1 to 1000:1 and the aqueous phase is visually distinct from and in physical contact with the oil phase.

In a second aspect, the present invention is directed to kit of parts comprises a cosmetic container, a multi-phase personal care composition of the present invention and instruction for use of the kit.

In a third aspect, the present invention is directed to a method for preparing a personal care product comprising the step of shaking a cosmetic container containing multi-phase personal care composition of the present invention by human hand.

In a fourth aspect, the present invention is directed to a method for providing skin lightening benefit to skin of an individual comprising the steps of (i) shaking a cosmetic container containing multi-phase personal care composition of the present invention by human hand and topically applying the resulting product.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

"Visually distinct" as used herein refers the regions occupied by each phase can be separately seen by human eye as distinctly separate regions in contact with one another (i.e., they are not emulsions or dispersions of particles of less than 100 microns).

"Multi-phase" as used herein refers to that at least two phases occupy separate and distinct physical spaces inside the container in which they are stored, but are in direct contact with one another (i.e., they are not separated by a barrier).

"Transparent" as used herein refers to that at least 70%, preferably at least 80%, more preferably at least 85% of light, having wavelength of 550 nm transmits a 1 cm thick of sample, measured by a UV-vis spectrometer (e.g. Perkin-Elmer Lambda 650S) at 25° C. "Opaque" as used herein refers to that no greater than 50%, preferably no greater than 30% of light transmits by same method.

Resorcinol derivative preferably refers to that at least one hydrogen on the ring structure and/or on a hydroxy group of the resorcinol replaced with an alkyl group, phenyl alkyl group. Preferably, the resorcinol derivative is 4-substituted resorcinol. The resorcinol derivative useful for the present invention preferably has the following formula (I):

(I)

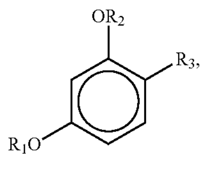

wherein each $R_1$ and $R_2$, independently, represents a hydrogen atom, $C_1$-$C_{18}$ alkyl group, $R_3$ represents an alkyl group or phenyl alkyl group having from 1 to 18 carbon atoms. In a preferred embodiment, both $R_1$ and $R_2$ represent hydrogen and $R_3$ represents an alkyl group or phenyl alkyl group having from 1 to 18 carbon atoms. More preferably, both $R_1$ and $R_2$ represent hydrogen, and $R_3$ represents an alkyl group or phenyl alkyl group having from 2 to 12 carbon atoms.

Preferably, the resorcinol derivative comprises 2-methylresorcinol, 4-chlororesorcinol, 4-methyl resorcinol, 4-ethyl resorcinol, 4-propyl resorcinol, 4-butyl resorcinol, 4-pentyl resorcinol, 4-hexyl resorcinol, 4-heptyl resorcinol, 4-octyl resorcinol, 4-nonyl resorcinol, 4-decyl resorcinol, phenylethyl resorcinol 4-acetylresorcinol, or a mixture thereof. More preferably, the resorcinol derivative comprises 2-methylresorcinol, 4-chlororesorcinol, 4-methyl resorcinol, 4-ethyl resorcinol, 4-propyl resorcinol, 4-butyl resorcinol, 4-pentyl resorcinol, 4-hexyl resorcinol, 4-heptyl resorcinol, 4-octyl resorcinol, 4-nonyl resorcinol, 4-decyl resorcinol, phenylethyl resorcinol 4-acetylresorcinol, or a mixture thereof. Even more preferably, the resorcinol derivative is selected from 4-ethyl resorcinol, 4-butyl resorcinol, 4-hexyl resorcinol, phenylethyl resorcinol, or a mixture thereof. Still even more preferably, the resorcinol derivative comprises 4-hexyl resorcinol. Most preferably resorcinol derivative is 4-hexyl resorcinol.

The amount of the resorcinol derivative is preferably in the range of 0.00001 to 10%, more preferably from 0.0001 to 8%, even more preferably from 0.001 to 5%, still even more preferably from 0.02 to 2%, most preferably from 0.1 to 0.6% by weight of the total amount of the composition. The amount of the resorcinol derivative is preferably in the range of 0.00001 to 15%, more preferably from 0.0001 to 10%, even more preferably from 0.001 to 7%, still even more preferably from 0.1 to 4%, most preferably from 0.5 to 2% by weight of the total amount of the oil phase.

Fatty ester as used herein refers to an ester having a straight chain with length of at least 6 carbon atoms, preferably at least 8 carbon atoms. The straight chain component of the fatty ester can be derived from a fatty acid, a fatty alcohol, or a combination thereof. In addition, the fatty ester can be a straight chain fatty ester, a branched chain fatty ester, a benzoate ester, or a combination thereof. Preferably, the fatty ester is a straight chain fatty ester, a branched chain fatty ester or a combination thereof. Preferably, the fatty ester is liquid at 25° C. and atmospheric pressure.

Preferably, the fatty ester is ester of carboxylic acids having 1 to 22 carbon atoms with an alcohol having 1 to 20 carbon atoms. Preferably, the carboxylic acids having 2 to 20 carbon atoms, more preferably 6 to 18, even more preferably 10 to 16 carbon atoms. Preferably the alcohol has 2 to 18, more preferably 3 to 15 carbon atoms. Preferably, the fatty ester is a monoester.

Preferably, the fatty ester comprises cetyl octanoate, stearyl heptanoate, stearyl caprylate, stearyl octanoate, lauryl octanoate, myristyl heptanoate, oleyl octanoate, myristyl propionate, cetyl acetate, cetyl propionate, cetyl octanoate, isodecyl neopentanoate, isopropyl myristate, isopropyl palmitate, isopropyl laurate, isopropyl linoleate, isopropyl tallowate, isopropyl ricinoleate, methyl laurate, methyl linoleate, methyl myristate, methyl stearate, methyl ricinoleate, methyl carprylate, methyl oleate, methyl palmitate, methyl behenate, methyl soyate, methyl tallowate, isopropyl behenate, isopropyl isostearate, isopropyl soyate, propyl oleate, butyl oleate, butyl stearate, methyl coconate, methyl lardate, isobutyl palmitate, butyl myristate, ethyl palmitate, ethyl myristate, ethyl oleate, ethyl stearate, isobutyl stearate, isobutyl myristate, isodecyl neopentanoate or mixtures thereof. More preferably, the fatty ester is selected from myristyl propionate, cetyl acetate, cetyl propionate, isodecyl neopentanoate, isopropyl myristate, isopropyl palmitate, isopropyl laurate, methyl laurate, methyl linoleate, methyl myristate, methyl stearate, methyl palmitate, isopropyl isostearate, butyl stearate, isobutyl palmitate, butyl myristate, ethyl palmitate, ethyl myristate, isobutyl stearate, isobutyl myristate, or a mixture thereof. Even more preferably, the fatty ester comprises myristyl propionate, cetyl propionate, isodecyl neopentanoate, isopropyl myristate, isopropyl palmitate, methyl myristate, methyl stearate, or a mixture thereof. Still even more preferably, the fatty ester comprises isopropyl myristate. Most preferably the fatty ester is isopropyl myristate.

The amount of the fatty ester is preferably in the range of 3 to 60%, more preferably from 8 to 55%, even more preferably from 15 to 50%, still even more preferably from 25 to 45%, most preferably from 28 to 42% by weight of the total amount of the composition. The amount of the fatty ester is preferably in the range of 10 to 98%, more preferably from 25 to 95%, even more preferably from 35 to 92%, still even more preferably from 45 to 80%, most preferably from 55 to 75% by weight of the total amount of the oil phase. The weight ratio of the fatty ester to the resorcinol derivative is from 10:1 to 1000:1, more preferably 20:1 to 500:1 and most preferably 50:1 to 300:1.

To improve the sensory of the composition, it is preferable that the composition additionally comprises volatile oil. The term "volatile oil" is understood to mean an oil capable of evaporating on contact with the skin in less than one hour, at 25° C. and atmospheric pressure. The volatile oil is a volatile liquid cosmetic oil having in particular a nonzero vapor pressure, at 25° C. and atmospheric pressure, especially having a vapor pressure ranging from 0.13 Pa to 40000 Pa, preferably ranging from 1.3 Pa to 13000 Pa and preferentially ranging from 1.3 Pa to 1300 Pa.

Preferred volatile oil comprises hydrocarbon volatile oil, volatile silicone oil or a mixture thereof. The hydrocarbon volatile oil is preferably $C_8$-$C_{16}$ isoalkanes. More preferably, the hydrocarbon volatile oil comprises isododecane, isodecane, isohexadecane or a mixture thereof. The term "silicone oil" is understood to mean an oil comprising at least one silicon atom and in particular comprising Si—O groups. The volatile silicone oils which can be used in the invention can be chosen in particular from silicone oils preferably having a flash point ranging from 40° C. to 102° C., more preferably 55 to 95° C. Preferred volatile silicone oils is linear or cyclic silicone oils having from 2 to 7 silicon atoms, optionally comprising alkyl or alkoxy groups having from 1 to 10 carbon atoms. Preferably the volatile silicone oils are selected from cyclopolydimethylsiloxanes (INCI name: cyclomethicone), such as cyclopentasiloxane, cyclohexasiloxane, octamethylcyclotetrasiloxane, decamethylcyclopentasiloxane or dodecamethylcyclohexasiloxane; linear silicones, such as heptamethylhexyltrisiloxane, heptamethyloctyltrisiloxane, hexamethyldisiloxane, octamethyltrisiloxane, decamethyltetrasiloxane or dodecamethylpentasiloxane, or a mixture thereof. More preferably, the volatile silicone oil is cyclopentasiloxane, cyclohexasiloxane or a mixture thereof.

Preferably, the volatile oil comprises isododecane, isodecane, isohexadecane, volatile dimethicone, cyclopentasiloxane, cyclohexasiloxane or a mixture thereof. More preferably the volatile oil is selected from isododecane, isodecane, isohexadecane cyclopentasiloxane, cyclohexasiloxane or a mixture thereof. Even more preferably, the volatile oil comprises isohexadecane.

The amount of the volatile oil is preferably in the range of 1 to 25%, more preferably from 8 to 55%, even more preferably from 3 to 18%, and most preferably from 6 to 12% by weight of the total amount of the composition. Preferably, the amount of volatile oil is 20 to 100%, more preferably 80 to 100% by weight of the total amount of fatty ester and volatile oil.

Preferably, the composition comprises retinoid. Typically, the retinoid is selected from retinyl ester, retinol, retinal, retinoic acid or a mixture thereof. More preferably the retinoid comprises retinol, retinyl ester, or a mixture thereof and even more preferably the retinoid is selected from retinol, retinyl ester, or a mixture thereof.

The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred retinol is all-trans-retinol, due to its wide commercial availability. Retinyl ester is an ester of retinol. The term "retinol" has been defined above. Retinyl esters suitable for use in the present invention are preferably $C_1$-$C_{30}$ esters of retinol, more preferably $C_2$-$C_{20}$ esters of retinol, and most preferably $C_2$, $C_3$, and $C_{16}$ esters of retinol. The retinyl ester for use in the present invention is preferably selected from retinyl palmitate, retinyl acetate, retinyl linoleate, retinyl oleate, retinyl propionate or a mixture thereof. More preferably the retinyl ester is selected from retinyl palmitate, retinyl acetate, retinyl propionate, or a mixture thereof. Most preferably the retinyl ester is selected from retinyl palmitate, retinyl propionate, or a mixture thereof.

Particularly preferred retinoid is selected from all-trans-retinol, retinyl palmitate, retinyl acetate, retinyl propionate, or a mixture thereof. Most preferably the retinoid is selected from retinyl palmitate, retinyl propionate, or a mixture thereof.

Preferably, retinoid is employed in the composition in an amount of 0.0001% to 8% by weight of the composition, more preferably in an amount of 0.0005% to 3%, even more preferably from 0.1 to 1% and most preferably in an amount of 0.2% to 0.8% by weight of the composition.

Preferably, the composition comprises a non-ionic surfactant. Preferably, the non-ionic surfactant comprises: a) the condensation products of aliphatic alcohols having from 8 to 22 carbon atoms in either straight or branched chain configuration with ethylene oxide, such as a coconut alcohol/ethylene oxide condensates having from 2 to 15 moles of ethylene oxide per mole of coconut alcohol; b) condensates of alkylphenols having C6-C15 alkyl groups with 5 to 25 moles of ethylene oxide per mole of alkylphenol; c) polyoxyethylene sorbitan fatty acid esters, for example polyoxyethylene sorbitan C6-24 fatty acid esters; d) alkyl glucoside, or a mixture thereof. More preferably the nonionic surfactant is alkyl glucoside. Alkyl glucoside as used herein includes alkyl polyglucosides.

Preferred alkyl glucoside is represented by formula of $RO-(G)_n$, wherein R is a branched or straight chain alkyl group which may be saturated or unsaturated, G is a saccharide group, and the degree of polymerisation, n, may have a value of from 1 to 10; Preferably R has a mean alkyl chain length of from $C_5$ to $C_{20}$, G is selected from $C_5$ or $C_6$ monosaccharide residues and n has a value of from 1 to 6; more preferably R has a mean alkyl chain length of from $C_6$ to $C_{16}$, G is glucose and n has a value of from 1 to 6.

More preferably the composition comprises fatty acid amide. Preferably, the fatty acid amide contains at least 6 carbon atoms. Suitable fatty acids include saturated and unsaturated, straight or branched fatty acids. Suitable fatty acids preferably contain from 8 to 24 carbon atoms, preferably from 12 to 20 carbon atoms, and most preferably from 12 to 18 carbon atoms, because longer chain fatty acid amides are more beneficial for conditioning of the skin. In the most preferred embodiment of the invention, amides of essential fatty acids are employed because essential fatty acids provide nutrition for the skin. Examples of essential fatty acids include but are not limited to linoleic, linolenic, arachidonic, gamma-linolenic, homo-gamma-linolenic, and mixtures thereof. Linoleic acid is most preferred because it is also a precursor to ceramide.

Amides suitable for use in the present invention may be simple amides (i.e., those containing a —$CONH_2$ group), N-alkyl amides, N,N-dialkyl amides, mono-alkanol amides, and di-alkanol amides. Suitable alkyl or alkanol groups contain from 1 to 30 carbon atoms, preferably from 1 to 20 carbon atoms, and most preferably from 1 to 8 carbon atoms. The preferred amides included in the present invention are mono- and di-alkanol amides, particularly of essential fatty acids. Alkanol amides are more commonly available than alkyl amides.

The preferred fatty acid amides are selected from mono- and diethanolamides of linoleic acid, palmitic acid, and coconut oil.

The fatty acid amide may be included in an amount ranging from 0.0001 to 10%, preferably from 0.01 to 4%, most preferably from 0.1 to 1% by weight of the total amount of the composition.

Preferably, the composition further comprises triglyceride. More preferably, the composition comprises caprylic/capric triglyceride, coconut oil, sunflower seed oil, safflower oil, cottonseed oil, olive oil or a mixture thereof. Particularly preferred triglyceride is caprylic/capric triglyceride. Preferably, the amount of triglyceride is 0.001 to 12%, more preferably 0.1 to 8%, even more preferably 0.5 to 5% by weight of the composition.

Preferably, the composition comprises polyhydric alcohol. Polyhydric alcohols may be selected from group of propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol or a mixture thereof. Most preferred polyhydric alcohol is glycerol known also as glycerin. The amount of polyhydric alcohol may range anywhere from 5 to 35%, preferably 8 to 25% and more preferably 12 and 18% by weight of the composition.

The composition may comprise water in amount of 10 to 90% by weight of the composition, more preferably from 15 to 78%, even more preferably from 20 to 65%, most preferably from 25 to 50% by weight of the composition.

The composition may comprise optional ingredients including moisturizing agent, skin lightening agent, preservatives, antioxidants, colorants, fragrance, or a combination thereof.

Vitamin B3 compounds (including derivatives of vitamin B3) e.g. niacin, nicotinic acid or niacinamide are the preferred skin lightening agent as per the invention, most preferred being niacinamide.

Preferably, the composition is a bi-phase liquid composition. Preferably, both the aqueous and oil phases are transparent. Preferably The weight ratio of the aqueous phase to the oil phase is preferably in the range of 1:8 to 8:1, more preferably 1:4 to 4:1, and even more preferably 1:2 to 2:1.

The multi-phase personal care composition can be provided to a consumer in any suitable way, but it is preferable that the composition is provided inside a cosmetics container. The cosmetics container preferably has a volume of 2 to 250 mL, more preferably 5 to 100 mL, even more preferably 8 to 60 mL and still even more preferably 10 to 50 mL.

Preferably a kit of parts comprises a cosmetic container, a multi-phase personal care composition according to the invention and instruction for use of the kit. Preferably, the instruction comprises the step of mixing aqueous phase with the oil phase by any suitable way, for example by shaking the container by human hand for at least 1 seconds, preferably 2 seconds to 5 minutes, more preferably 3 seconds to 1 minutes. Thus, a homogeneous personal care product is formed. Preferably the personal care product is opaque.

Preferably, the multi-phase personal care composition is capable of generating a personal care product by shaking the cosmetic container by human hand, preferably for 1 second to 5 minutes, more preferably 1 second to 1 minutes. Preferably, the personal care product is capable of recovering to be a multi-phase personal care composition by standing for 3 minutes to 20 hours, more preferably 10 minutes to 7 hours, and even more preferably 15 minutes to 4 hours.

Preferably, the personal care composition (product) is a skin care composition (product). The skin care composition (product) refers to a composition (product) suitable for topical application to human skin, preferably is a leave-on product. The term "leave-on" as used with reference to compositions herein means a composition that is applied to or rubbed on the skin, and left thereon. The term "skin" as used herein includes the skin on the face (except eye lids and lips), neck, chest, abdomen, back, arms, under arms, hands, and legs. Preferably "skin" means includes the skin on the face (except eye lids and lips) and under arms, more preferably skin means skin on the face other than lips and eyelids.

The following examples are provided to facilitate an understanding of the invention. The examples are not intended to limit the scope of the claims.

EXAMPLES

Example 1

This example demonstrates the preparation of multi-phase skin care composition.

TABLE 1

| Phase | Ingredient | Samples (wt %)* A | 1 | 2 |
|---|---|---|---|---|
| Aqueous | Deionized Water | To 100 | To 100 | To 100 |
| | Glycerin | 15.0375 | 15.0375 | 15.0375 |
| | Disodium EDTA | 0.050 | 0.050 | 0.050 |
| | Cocamide MEA | 0.2125 | 0.2125 | 0.2125 |
| | Caprylyl/Capryl Glucoside | 1.240 | 1.240 | 1.240 |
| | Niacinamide | 3.000 | 3.000 | 3.000 |
| | Phenoxyethanol | 0.600 | 0.600 | 0.600 |
| | Iodopropynyl butylcarbamate | 0.006 | 0.006 | 0.006 |
| | Sodium Chloride | 0.600 | 0.600 | 0.600 |
| Oil | Isohexadecane [a] | 35.47 | 9.74 | |
| | Isopropyl Myristate [b] | — | 29.23 | 35.47 |
| | Caprylic/Capric Triglyceride [c] | 3.500 | — | 3.500 |
| | Retinol Propionate | 0.3168 | 0.3168 | 0.3168 |
| | Hexyl Resorcinol [d] | 0.400 | 0.400 | 0.400 |
| | Fragrance | 0.200 | 0.200 | 0.200 |

*The level of the ingredients refers the level of active.
[a] IPM-R, supplied by Kokyu alcohol kogyo Co. Ltd.
[b] Arlamol HD, supplied by Croda.
[c] Crodamol GTCC, supplied by Croda.
[d] Vivinol-HR, supplied by Clariant.

The samples in Table 1 were prepared by mixing Cocamide MEA at a temperature of 50 to 60° C., cooling down to room temperature, and adding other ingredients to get the aqueous phase. The ingredients for oil phase were mixed together to get the oil phase. The sample were obtained by mixing the aqueous phase and oil phase.

Example 2

This example demonstrates the incorporation of fatty ester improves discoloration of multi-phase skin care composition.

The samples A, 1 and 2 were prepared as described in Example 1. All three samples are colorless and transparent. Then, they were packaged into three identical transparent jars with equal amount. These packaged samples were placed into cabinets with pre-set temperatures of 50° C. for four weeks. Table 2 shows the color change after storage.

TABLE 2

| Sample | Color 0 day | 50° C. for four weeks |
|---|---|---|
| A | Colorless | Crimson |
| 1 | Colorless | Yellow |
| 2 | Colorless | Light Yellow |

As shown in Table 2, the discoloration problem of the multi-phase composition comprising resorcinol derivative was significantly improved by including fatty ester into the multi-phase composition.

The invention claimed is:

1. A multi-phase personal care composition comprising:

(a) an aqueous phase, and (b) an oil phase comprising fatty ester and resorcinol derivative, wherein the fatty ester to the resorcinol derivative is present in a weight ratio of from 10:1 to 1000:1 and the aqueous phase is visually distinct from and in physical contact with the oil phase.

2. The multi-phase personal care composition according to claim 1, wherein the resorcinol derivative is selected from 4-ethyl resorcinol, 4-butyl resorcinol, 4-hexyl resorcinol, phenylethyl resorcinol, or a mixture thereof.

3. The multi-phase personal care composition according to claim 1, wherein the resorcinol derivative is present in amount of 0.00001 to 10% by weight of the total amount of the composition.

4. The multi-phase personal care composition according to claim 1, wherein the fatty ester is an ester of carboxylic acids having 1 to 22 carbon atoms with an alcohol having 1 to 20 carbon atoms and wherein the fatty ester is present in the amount of 3 to 60%.

5. The multi-phase personal care composition according to claim 1, wherein the fatty ester is present in amount of 28 to 42% by weight of the total amount of the composition.

6. The multi-phase personal care composition according to claim 1, wherein the fatty ester to the resorcinol derivative is in present in a weight ratio of 50:1 to 300:1.

7. The multi-phase personal care composition according to claim 1, wherein the composition additionally comprises volatile oil selected from isododecane, isodecane, isohexadecane cyclopentasiloxane, cyclohexasiloxane, or a mixture thereof.

8. The multi-phase personal care composition according to claim 1, wherein the composition further comprises triglyceride.

9. The multi-phase personal care composition according to claim 1, wherein the composition comprises a retinoid.

10. The multi-phase personal care composition according to claim 1, wherein both the aqueous phase and oil phase are transparent.

11. The multi-phase personal care composition according to claim 1, wherein the aqueous phase to the oil phase is present in a weight ratio of 1:8 to 8:1.

12. A kit of parts comprising a cosmetic container, a multi-phase personal care composition according to claim 11, and instruction for use of the kit.

13. A method for preparing a personal care product comprising the step of shaking a cosmetic container containing the multi-phase personal care composition according to claim 1, by human hand.

14. A method for providing skin lightening benefit to skin of an individual comprising the steps of i) shaking a cosmetic container containing the multi-phase personal care composition according to claim 1, by human hand and ii) topically applying the resulting product.

15. The multi-phase personal care composition according to claim 2, wherein the resorcinol derivative comprises 4-hexyl resorcinol and further wherein the resorcinol derivative is present in amount of 0.001 to 5% by weight of the total amount of the composition.

16. The multi-phase personal care composition according to claim 3, wherein the resorcinol derivative is present in amount of 0.1 to 0.6% by weight of the total amount of the composition.

17. The multi-phase personal care composition according to claim 4, wherein the fatty ester comprises isopropyl myristate.

18. The multi-phase personal care composition according to claim 8, wherein the composition further comprises triglyceride in amount of 0.001 to 12% by weight of the composition.

19. The multi-phase personal care composition according to claim 9, wherein the retinoid comprises retinyl palmitate, retinyl propionate, or a mixture thereof.

20. The multi-phase personal care composition according to claim 1, wherein the aqueous phase to the oil phase is present in a weight ratio of 1:2 to 2:1.

* * * * *